US006020537A

United States Patent [19]
Prusiner

[11] Patent Number: 6,020,537
[45] Date of Patent: *Feb. 1, 2000

[54] PRION PROTEIN STANDARD AND METHOD OF MAKING SAME

[75] Inventor: Stanley B. Prusiner, San Francisco, Calif.

[73] Assignee: The Regents of the University of California, Oakland, Calif.

[*] Notice: This patent is subject to a terminal disclaimer.

[21] Appl. No.: 09/199,523

[22] Filed: Nov. 25, 1998

Related U.S. Application Data

[63] Continuation-in-part of application No. 08/935,363, Sep. 22, 1997, which is a continuation-in-part of application No. 08/692,892, Jul. 30, 1996, Pat. No. 5,792,901, which is a continuation-in-part of application No. 08/521,992, Aug. 31, 1995, Pat. No. 5,908,969, which is a continuation-in-part of application No. 08/509,261, Jul. 31, 1995, Pat. No. 5,763, 740, which is a continuation-in-part of application No. 08/242,188, May 13, 1994, Pat. No. 5,565,186.

[51] Int. Cl.$^7$ ............................. C07K 14/00; C12N 15/00
[52] U.S. Cl. ................................... 800/18; 800/4; 800/13; 530/350
[58] Field of Search .................................. 800/13, 4, 18; 514/2; 530/350

[56] References Cited

U.S. PATENT DOCUMENTS 5,792,901   8/1998   Prusiner et al. ........................... 800/13

FOREIGN PATENT DOCUMENTS

WO 91/19810   12/1991   WIPO .
WO 93/10227   5/1995    WIPO .

OTHER PUBLICATIONS

Baker, H.F., et al. "Aminoacid Polymorphism in Human Prion Protein and Age at Death in Inherited Prion Disease," *Lancet* (1991) 337:1286.
Barry, R.A., et al., "Monoclonal Antibodies to the Cellular and Srapie Prion Proteins," *J. Infect. Dis.* (1986) 154(3):518–521.
Basler et al., "Scrapie and Cellular PrP Isoforms Are Encoded by the Same Chromosomal Gene," *Cell*, (1986) 46:417–28.
Berger, J.R., et al., "Creutzfeldt–Jakob disease in a physician: A review of the disorder in health care workers", *Neurology*, (1993) 43:205–206.
Bolton et al., "Identification of a Protein That Purifies with the Scrapie Prion," *Science* (1982) 218: 1309–11.
Brown et al., "Friendly Fire in Medicine: Hormones, Homografts, and Cruetzfeldt–Jakob Disease," *Lancet* (1992) 340: 24–27.
Buchanan et al., "Mortality, Neoplasia, and Creutzfeld–Jakob Disease in Patients Treated with Human Pituitary Growth Hormone in the United Kingdom", *BMJ* (1991) 302:824–828.
Bueler et al., "Mice Devoid of PrP are Resistant to Scrapie," *Cell* (1993) 73:1339–1347.

Bueler et al., "Normal Development and Behavior of Mice Lacking the Neuronal Cell–surface PrP Protein," *Nature* (1992) 356:577–582.
Carlson et al., "Linkage of Protein and Scrapie Incubation Time Genes," *Cell* (1986) 46:503–511.
Chandler, "Encephaolpathy in Mice Produced by Inoculation with Scrapie Brain Material," Lancet (1961) 1:1378–79.
Cochius et al, "Creutzfeldt–Jakob Disease in a Recipient of Human Pituitary–Derived Gonadotrophin: A Second Case," *J. Neurol. Neurosurg. Psychiatry* (1992) 55:1094–1095.
Cochius et al., "Creutzfeldt–Jakob Disease in a Recipient of Human Pituitary–Derived Gonadotrophin," *Aust. N.Z. J. Med.* (1990) 20:592–593.
Collinge et al., "Genetic Predisposition to Latrogenic Creutzfeldt–Jakob Disease," *Lancet* (1991) 337:1441–1442.
Cousens, S.N., et al., "Geographical distribution of cases of Creutzfeldt–Jakob disease in England and Wales 1970–84", *J. Neurol. Neurosurg. Psychiatry* (1990) 53:459–465.
Farlie, P.G., et al., "bcl–2 Transgene expression can protect neurons against developmental and induced cell death", *Proc. Natl. Acad. Sci. USA* (1995) 92:4397–4401.
Gabriel et al., "Molecular Cloning of a Candidate Chicken Prion Protein," *Proc. Natl. Acad. Sci. USA* (1992) 89:9097–9101.
Gajdusek, D.C., "Unconventional Viruses and the Origin and Disappearance of Kuru," *Science* (1977) 197:943–960.
Gibbs, Jr. et al., "Creutzfeldt–Jakob Disease Infectivity of Growth Hormone Derived from Human Pituitary Glands," *N.Eng. J. Med.* (1993) 328:358–359.
Goldfarb et al, "Fatal Familial Insomnia and Familial Creutzfeldt–Jakob Disease: Disease Phenotype Determined by a DNA Polymorphism," *Science* (1992) 258:806–808.
Goldmann et al., "Two Alleles of a Neural Protein Gene Linked to Scrapie in Sheep," *Proc. Natl. Acad. Sci. USA* (1990) 87:2476–2480.
Goldmann et al., "Different Forms of the Bovine PrP Gene Have Five or Six Copies of a Short, G–C Rich Element within the protein–coding Exon," *J. Gen. Virol.* (1991) 72:201–204.
Harris et al., "A Prion–like Protein from Chicken Brain Copurifies with an Acetylcholine Receptor–Inducing Activity," *Proc. Natl. Acad. Sci. USA* (1991) 88:7664–7668.

(List continued on next page.)

*Primary Examiner*—Bruce R. Campell
*Assistant Examiner*—Anne-Marie Baker
*Attorney, Agent, or Firm*—Dianna L. DeVore; Bozicevic, Field & Francis LLP

[57] ABSTRACT

The invention provides prion protein standards for use as reference materials for prion detection. The standard may be species specific, i.e. the standard is comprised of a preparation for detection of a single strain prion or it may be prepared to allow detection of multiple prion strains simultaneously. The invention also provides methods of preparing the prion protein standards using a group of non-human host mammals which have their genome manipulated with respect to genetic material related to a PrP gene such that the mammals are susceptible to infection with a prion which generally only infects an animal which is genetically diverse from the host.

31 Claims, No Drawings

OTHER PUBLICATIONS

Hasty, P., et al., "Introduction of a subtle mutation into the Hox–2.6 locus in embryonic stem cells", *Nature* (1991) 350:243–246.

Healy et al., "Creutzfeldt–Jakob Disease After Pituitary Gonadotrophins: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Hsaio et al., "Linkage of a Prion Protein Missense Variant to Gerstmann–Straussler Syndrome," *Nature* (1989) 383:342–345.

Hsaio et al., "A Prion Protein Variant in a Family with the Telencephalic Form of Gerstmann–Strussler–Scheinker Syndrome," *Neurology* (1991) 41:681–684.

Hsaio et al., "Inherited Human Prion Diseases," *Neurology* (1990) 40:1820–1827.

Kascsak, R.J., et al., "Mouse Polyclonal and Monoclonal Antibody to Scrapie–Associated Fibril Proteins," *J. Virol.* (1987) 61(12):3688–3693.

Koch et al., "Creutzfeldt–Jakob Disease in a Young Adult with Idiopathic Hypopituitarism," *N. Engl. J. Med.* (1985) 313:731–733.

Kretzschmar et al., "Molecular Cloning of a Human Prion Protein cDNA," *DNA* (1986) 5:315–324.

Kretzschmar et al., "Molecular Cloning of a Mink Prion Protein Gene," *J.Gen.Virol.* (1992) 73:2757–2761.

Lasmezas et al.,"Recombinant Human Growth Hormone and Insulin–Like Growth Factor I Induce PRP Gene Expression in PC12 Cell," *Biochem. Biophys. Res.Commun.* (1993) 196:1163–1169.

Locht et al., "Molecular Cloning and Complete Sequence of Prion Protein cDNA from Mouse Brain Infected with the Scrapie Agent," *Proc. Natl. Acad. Sci. USA* (1986) 83:6372–6276.

Manuelidis et al., "Serial Propagation of Creutzfeldt–Jakob Disease in Guinea Pigs," *Proc. Natl. Acad. Sci. USA* (1976) 73:223–227.

Manuelidis et al., "Interspecies Transmission of Creutzfeldt– Jakob Disease to Syrian Hamsters with Reference to Clinical Syndromes and Strain of Agent," *Proc. Natl. Acad. Sci USA* (1978) 75:3432–3436.

McKinley et al, "A Protease–Resistant Protein is a Structural Component of the Scrapie Prion," *Cell* (1983) 35:57–62.

Medori et al., "Fatal Familial Insomia, a Prion Disease with a Mutation at Codon 178 of the Prion Protein Gene," *N. Engl.J. Med.* (1992) 326:444–449.

Muramoto, T., et al., "The Sequential Development of Abnormal Prion Protein Accumulation in Mice with Creuzfeldt–Jakob Disease," *Am. J. Pathol.* (1992) 140(6):1411–1420.

Nisbet et al., "Creutzfeldt–Jakob Disease in a Second Patient Who Received a Cadaveric Dura mater Graft," *J.Am. Med.Assoc.* (1989) 261:1118.

Palmer, M.S., et al., "Homozygous Prion Protein Genotype Predisposes to Sporadic Creutzfeldt–Jakob Disease", *Nature* (1991) 352:340–342.

Patel, "France Reels at Latest Medical Scandal," *New Scientist*, Jul. 31, 1993, p. 4.

Patel, "Placenta Donors to be Screened for Brain Disease," *New Scientist*, Nov. 20, 1993, p. 10.

Pan, K.M., et al., "Conversion of β–sheets features in the formation of the scrapie prion proteins", *Proc. Natl. Acad. Sci. USA* (1993) 90:10962–10966.

Prusiner et al., "Measurement of the Scrapie Agent Using an Incubation Time Interval Assay," *Annals. Neurol.* (1982) 11(4):353–358.

Prusiner et al., "Further Purification and Characterization of Scrapie Prions," *Biochemistry* (1982) 21:2942–50.

Prusiner, S.B., et al., "Scrapie Prions Aggregate to Form Amyloid–like Birefringent Rods," *Cell* (1983) 35:349–358.

Prusiner et al., "Transgenic Studies Implicate Interactions Between Homologous PrP Isoforms in Scrapie Prion Replication," *Cell* (1990) 63:673–686.

Prusiner et al., "Molecular Biology of Prion Diseases," *Science* (1991) 252:1515–1522.

Prusiner, S.B. "Molecular Biology of Prions Causing Infectious and Genetic Encephalopathies of Humans as well as Scrapie of Sheep and BSE of Cattle." *Develop. Biol. Standard.* (1991) vol. 75, pp. 55–74, especially p. 65.

Prusiner et al., "Ablation of the Prion Protein (PrP) Gene in Mice Prevents Scrapie and Facilitates Production of Anti–PrP Antibodies," *Proc. Natl. Acad. Sci. USA* (1993) 90:10608–10612.

Prusiner, S.B., et al., "Immunologic and Molecular Biological Studies of Prion Proteins in Bovine Spongiform Encephalopathy," *J. Infect. Dis.* (1993) 167:602–613.

Prusiner et al., "Prion Diseases and Neurodegeneration," *Ann.Rev.Neurosci.* (1994) 17:311–339.

Raeber et al., "Attempts to Convert the Cellular Prion Protein into the Scrapie Isoform in Cell–Free Systems," *J. Virol.* (1992) 66:6155–6163.

Ridley et al., *Lancet* Occupational Risk of Creuzfeldt–Jakob Disease, (1993) 341:641–2.

Rogers, M. et al., "Epitope Mapping of the Syrian Hamster Prion Protein Utilizing Chimeric and Mutant Genes in a Vaccinia Virus Expression System," *J. Immunol.* (1991) 147(10):3568–3574.

Scott, M., et al, "Transgenic Mice Expressing Hamster Prion Protein Produce Species–Specific Infectivity and Amyloid Plaques," *Cell* (1989) 59:847–857.

Scott et al, "Chimeric Prion Protein Expression in Cultured Cells and Transgenic Mice," *Protein Sci.* (1992) 1:986–97.

Scott et al, "Propagation of Prions with Artificial Properties in Transgenic Mice Expressing Chimeric PrP Genes," *Cell* (1993) 73:979–988.

Serban, D., et al. "Rapid detection of Creutzfeldt–Jakob disease and scrapie prion proteins", *Neurology* (1990) 40:110–117.

Stahl et al., "Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi, J. et al., "Developments in Diagnosis for Prion Diseases," *Br. Med. Bull.* (1993) 49(4):971–979.

Tateishi et al.,"Transmission of Chronic Spongiform Encephalopathy with Kuru Plaques from Humans to Small Rodents," *Ann.Neurol.* (1979) 5:581–584.

Telling, G.C. et al. "Prion Propagation in Mice Expressing Human and Chimeric PrP Transgenes Implicates the Interaction of Cellular PrP with Another Protein." *Cell* Oct. 6, 1995, vol. 83, pp. 79–90, especially p. 84.

Thadani et al., "Creutzfeldt–Jakob Disease Probably Acquired From a Cadaveric Dura Mater Graft," *J. Neurosurg.* (1988) 69:766–769.

Valancius, V. and Smithies, O., "Testing and "In–Out" Targeting Procedure for Making Subtle Genomic Modifications in Mouse Embryonic Stem Cells", *Mol. Cell Biol.* (1991) 11(3):1402–1408.

Westaway et al., Homozygosity for Prion Protein Alleles Encoding Glutamine–171 Renders Sheep Susceptible to Natural Scrapie,: *Genes Dev.* (1994) 8:959–969.

Westaway et al., "Degeneration of Skeletal Muscle, Peripheral Nerves, and the Central Nervous System in Transgenic Mice Overexpressing Wild–Type Prion Proteins," *Cell* (1994) 76:117–129.

Willison et al., "Creutzfeldt–Jakob Disease Following Cadaveric Dura Mater Graft," *Neurosurg. Psychiatric* (1991) 54:940.

Wilesmith, J.W., "The epidemiology of bovine spongiform encephalopathy", *Acad. Press.* (1991) 2:239–245.

Caughey et al. In vitro expression in eukaryotic cells of a prion protein gene cloned from scrapie–infected mouse brain. Proc. Natl. Acad. Sci. USA 85:4657–4661, Jul. 1988.

Hammer et al. Spontaneous inflammatory disease in transgenic rats expressing HLA–B27 and human B2m: An animal model of HLA–B27–associated human disorders. Cell 63: 1099–1112, Nov. 1990.

Scott et al. Transgenic mice expressing hamster prion protein produce species–specific scrapie infectivity and amyloid plaques. Cell 59: 847–857, Dec. 1989.

Wall, RJ Transgenic livestock: Progress and prospects for the future. Theriogenology 45: 57–68, 1996.

PRION PROTEIN STANDARD AND METHOD OF MAKING SAME

CROSS-REFERENCE TO RELATED APPLICATIONS

This application is a continuation-in-part of our earlier filed application Ser. No. 08/935,363, filed Sep. 22, 1997 pending, which is a continuation-in-part of our earlier filed application Ser. No. 08/692,892, filed Jul. 30, 1996 now issued U.S. Pat. No. 5,792,901 which is a continuation-in-part of our earlier filed application Ser. No. 08/521,992, filed Aug. 31, 1995, now U.S. Pat. No. 5,908,969 which is a continuation-in-part of our earlier filed application Ser. No. 08/509,261, filed Jul. 31, 1995 now issued U.S. Pat. No. 5,763,740 which is a continuation-in-part of our earlier filed application Ser. No. 08/242,188, filed May 13, 1994 now issued U.S. Pat. No. 5,565,186 to which we claim priority under 35 U.S.C. §120 and which are incorporated herein by reference in their entirety.

GOVERNMENT RIGHTS

The United States Government may have certain rights in this application pursuant to Grant No. NS 14069, AGO2132, NS22786, AGO8967 and AG10770 awarded by the National Institutes of Health.

FIELD OF THE INVENTION

This invention relates to the field of bioassays and more particularly to standards for assays for isolating and detecting a disease conformation of a protein present in a sample also containing a non-disease conformation of the protein, and method of making such standards.

BACKGROUND OF THE INVENTION

Prions are infectious pathogens that cause invariably fatal prion diseases (spongiform encephalopathies) of the central nervous system in humans and animals. Prions differ significantly from bacteria, viruses and viroids. The dominating hypothesis is that no nucleic acid is necessary to allow for the infectivity of a prion protein to proceed.

A major step in the study of prions and the diseases they cause was the discovery and purification of a protein designated prion protein [Bolton, McKinley et al. (1 982) *Science* 218:1309–1311; Prusiner, Bolton et al. (1982) *Biochemistry* 21:6942–6950; McKinley, Bolton et al. (1983) *Cell* 35:57–62]. Complete prion protein-encoding genes have since been cloned, sequenced and expressed in transgenic animals. $PrP^C$ is encoded by a single-copy host gene [Basler, Oesch et al. (1986) *Cell* 46:417–428] and when $PrP^C$ is expressed it is generally found on the outer surface of neurons. Many lines of evidence indicate that prion diseases result from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher β-sheet and lower α-helix content [Pan, Baldwin et al. (1993) *Proc Natl Acad Sci USA* 90:10962–10966; Safar, Roller et al. (1993) *J Biol Chem* 268:20276–20284]. The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiform encephalopathies) and it is a critical factor in neuronal degeneration [Prusiner (1997) The Molecular and Genetic Basis of Neurological Disease, 2nd Edition 103–143]. The most common prion diseases in animals are scrapie of sheep and goats and bovine spongiform encephalopathy (BSE) of cattle [Wilesmith and Wells (1991) *Curr Top Microbiol Immunol* 172:21–38]. Four prion diseases of humans have been identified: (1) kuru, (2) Creutzfeldt-Jakob Disease (CJD), (3) Gerstmann-Straussler-Sheinker Disease (GSS), and (4) fatal familial insomnia (FFI) [Gajdusek (1977) *Science* 197:943–960; Medori, Tritschler et al. (1992) *N Engl J Med* 326:444–449]. Initially, the presentation of the inherited human prion diseases posed a conundrum which has since been explained by the cellular genetic origin of PrP.

Prions exist in multiple isolates (strains) with distinct biological characteristics when these different strains infect in genetically identical hosts [Prusiner (1997) The Molecular and Genetic Basis of Neurological Disease, 2nd Edition: 165–186]. The strains differ by incubation time, by topology of accumulation of $PrP^{Sc}$ protein, and in some cases also by distribution and characteristics of brain pathology [DeArmond and Prusiner (1997) Greenfield's Neuropathology, 6th Edition:235–280]. Because $PrP^{Sc}$ is the major and very probably the only component of prions, the existence of prion strains has posed a conundrum as to how biological information can be enciphered in a molecule other than one comprised of nucleic acids. The partial proteolytic treatment of brain homogenates containing some prion isolates has been found to generate peptides with slightly different electrophoretic mobilities [Bessen and Marsh (1992) *J Virol* 66:2096–2101; Bessen and Marsh (1992) *J Gen Virol* 73:329–334; Telling, Parchi et al. (1996) *Science* 274:2079–2082]. These findings suggested different proteolytic cleavage sites due to the different conformation of $PrP^{Sc}$ molecules in different strains of prions. Alternatively, the observed differences could be explained by formation of different complexes with other molecules, forming distinct cleavage sites in $PrP^{Sc}$ in different strains [Marsh and Bessen (1994) *Phil Trans R Soc Lond B* 343:413–414]. Some researchers have proposed that different prion isolates may differ in the glycosylation patterns of prion protein [Collinge, Sidle et al. (1996) *Nature* 383:685–690; Hill, Zeidler et al. (1997) *Lancet* 349:99–100]. However, the reliability of both glycosylation and peptide mapping patterns in diagnostics of multiple prion strains is currently still debated [Collings, Hill et al. (1997) *Nature* 386:564; Somerville, Chong et al. (1997) *Nature* 386:564].

A number of methods exist for the detection of a protein in a sample, and specifically for the detection of $PrP^{Sc}$. Assays to detect $PrP^{Sc}$ are described in U.S. Pat. Nos. 5,565,186 and 5,792,901 and U.S. patent application Ser. No. 08/935,363, incorporated herein by reference, which describe and disclose immunoassay methods for determining the presence of $PrP^{Sc}$ in a sample. Quality assurance, quality control, and reagent documentation are all critical issues in determining the presence of infectious prions in a sample. Variation between assays can be reduced by the use of a common standard for the calibration of the different methods. The basis of a calibration system is a primary standard sample that provides both high sensitivity and reproducibility of detection to effectively and consistently analyze different samples. A standard is indispensable in assigning an accurate target value to reference materials in an assay method. Standards are also useful in testing reagents used in assays for reliability and effectiveness.

There is a method of providing standardized, cost-effective assays for reproducibly testing sample materials for the presence of a prion protein. Accordingly, there is a need for standards for the calibration of assays to detect prions and as controls in the assays, to ensure high sensitivity and to reduce problems of irreproducibility between different samples, and to test the quality of reagents used in the assays.

SUMMARY OF THE INVENTION

The invention provides prion protein standards for use as reference materials in assays to detect prion proteins in a sample, e.g. determine the presence of prions in a sample from a mammalian brain. The standard is preferably specific to prions which infect a single species and more preferably may be specific to a single infectious strain. However, the standardized preparation may include multiple strains and allow for detection of multiple prion strains simultaneously.

In one embodiment, the invention features a standard produced from a preparation of brains from a plurality of transgenic host mammals genetically manipulated to allow infection by prions which normally only infect a genetically diverse species, i.e. would generally only effect an animal with a significantly different PrP gene. The host animals are inoculated with prions from the genetically diverse species, the brains homogenized, and the sample standardized. The preparations may be standardized in accordance with a number of characteristics, e.g. by controlling level of infection, time from inoculation until disease symptoms are noted, genetic background, the concentration of prions and the like. In addition, prions isolated from infected animals may be used to ensure consistency of prion concentration in a standardized background by spiking the prion preparation with prions may be (a) produced synthetically, (b) isolated from transgenic animals, and/or (c) obtained from cadavers.

In another embodiment, the standard is comprised of isolated prions introduced to a homogenized preparation of brain. The isolated prions may be initially produced by transgenic host mammals. These transgenic animals have their genome manipulated with respect to genetic material related to a PrP gene such that the animals are susceptible to infection with a prion which generally only infects an animal which is genetically diverse from the host transgenic mammals used to produce the prion proteins. The transgenic animals are inoculated with prions of a genetically diverse species. After sufficient incubation time, prions are isolated from the transgenic animals and the isolated prions are introduced to a homogenized brain preparation. Preferably, the brain preparation is of a species genetically similar and more preferably genetically the same as the species susceptible to infection by the isolated prion proteins.

In yet another embodiment of the invention, a plurality of different standards are assembled to create a kit which is useful as a standard for multiple prion strains. These samples have many uses, for example, to test for the specificity of an agent, e.g. an antibody, that recognizes $PrP^{Sc}$. However, the standardized preparation is preferably used in the creation of a positive control when using transgenic animals and/or immunoassays to test samples for prions. Prion standards containing prions from a plurality of different species can be used to test cross-reactivity of the agent between species. The different samples can be dispersed within a single agglomerated sample, and the specificity determined by the strength of the $PrP^{Sc}$ recognition, or the standards may be in a discrete assembly, allowing the elucidation of reactivity to a standard of a specific species.

The invention also provides methods of preparing the prion protein standards. To produce the prion protein standard it is necessary to produce a group of non-human host mammals which each have their genome manipulated in an identical manner with respect to genetic material related to a PrP gene such that the mammals are susceptible to infection with a prion which generally only infects an animal which is genetically diverse from the host. The transgenic host animals produced are inoculated with a prion containing composition that infects the genetically diverse animal, and the animals are observed until they exhibit symptoms of prion infection. Brain or other tissue is harvested from the animals and homogenized to create the prion standard. This process is repeated, using homogenized brain tissue of a standardized preparation of a previously inoculated group to inoculate a new group, to further reduce variability in the production of the standard. Preferably, the inocula is from the group just prior to the new group. Different forms of transgenic animals can be used in the production of different preparations and two or more different standardized preparations can be mixed. However, it is preferable to produce the preparation using genotypically similar non-human mammals with endogenous PrP gene ablated and having operatively inserted into its genome one or more of the following: an exogenous PrP gene from a genetically diverse species; an artificial PrP gene which includes a portion of the PrP gene of a genetically diverse species; and an artificial PrP gene with critical codons from a genetically diverse species.

The invention also features a method of using a standard of the invention as a positive control in a prion protein assay. The assay may be a bioassay which uses transgenic animals (e.g. see U.S. Pat. No. 5,792,901 issued Aug. 11, 1998) or an immunoassay (e.g. see PCT UC96/12510). The standards function to ensure reproducibility and specificity of an assay by functioning as a reference material with a known and consistent level of prion protein concentration. The standards also make it possible to determine sensitivity and to adjust selectivity relative to sensitivity as needed.

The invention also features a method of calibrating an assay using the standards of the invention. Calibration can be within a single assay, to determine efficacy at a given level of prion protein concentration, or between assays, to allow comparison of results of different assays by adjusting detection levels between assays. For example, if one assay is more sensitive than another, calibration with a standard can be used to determine the factor for converting measured levels to corrected levels for comparison of results obtained using the different assays.

The invention also features a method of determining the quality of reagents used in a prion protein assay by testing the reagents using standards of the invention. The standards provide a consistent prion protein concentration and preferably a consistent background. Testing reagents against the standard can ensure selectivity and/or reproducibility of a reagent used in an assay.

The invention further provides a kit containing the standard and reagents needed to practice different types of bioassays and immunoassays. The reagents will vary depending on the assay, e.g. the reagents in an immunoassay may include the 3F4 antibody and/or the R2 antibody as well as the standard. The kit may contain standards for different prion strains and/or with different concentrations of prions that infect a single species of animal. Alternatively, the kit could contain standards for multiple species preferably with the same known amount of prions in each standard, more preferably with each standard containing one or more infectious unit of prion proteins.

An object is to provide a standard generated from standardized prion preparation produced from harvested brain tissue taken from animals that have substantially identical genomes and specifically have substantially identical genetic material related to prions, which animals exhibit symptoms (in 250 days or less) of prion infection after being inoculated with prions which generally only infect a genetically diverse species.

A feature of the invention is that the standard itself may be used to inoculate new animals for the production of an additional prion standard. This allows reproducibility of the standard between different batches, minimizes variability between different batches of the standard, and allows for genetic homogeneity in the background used with the standard.

An advantage of the invention is that the prion standard can eliminate the need for extracting brain tissue from individual mammals for use as positive controls in prion assays. Currently, control animals may have been infected with different types of prions and may each have a different genetic make up regarding genetic material related to prions. The use of a prion standard eliminates the variability of the control, both within a single experiment and between assays.

Another advantage is that prion assays can be carried out more reproducibly using assays calibrated by the prion standard of the invention.

Another advantage is that the prion standard will allow comparison of $PrP^{Sc}$ levels determined by different prion assays.

Another advantage is that the prion standard will reduce variability of prion assays, both within a single experiment and between multiple assays.

A feature of the present invention is that the plurality of transgenic and/or hybrid animals used to make the prion standard injected with a sample containing pathogenic prions will consistently develop the disease effects of the prions within a relatively short time, e.g. about 200 days±50 days after injection or less.

Another feature of the invention is that the transgene used in the production of the standard can be chosen to reflect any polymorphisms and/or mutations of the test material, resulting in a standard that is genetically similar to the test material.

These and other objects, advantages and features of the invention will become apparent to those skilled in the art upon reading this disclosure.

DETAILED DESCRIPTION OF THE PREFERRED EMBODIMENTS

Before the present standards and methods are disclosed and described, it is to be understood that this invention is not limited to particular antibodies, proteins, labels, assays or methods as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application. Nothing herein is to be construed as an admission that the present invention is not entitled to antedate such publication by virtue of prior invention. Further, the dates of the publications provided are subject to change if it is found that the actual date of publication is different from that provided here.

DEFINITIONS

The term "standard", "prion protein standard", "prion standard" and the like as used herein refers to a preparation for prion assays in which the level of prion infection and background characteristics are sufficiently established to allow the standard to function as a reference material, e.g., for prion immunoassays and/or prion bioassays. Such a standard is produced using the procedure of the invention, and the resulting standard is reliable for both precision and accuracy in assays for determining prion concentration, infectivity, and the like.

The term "reference material" is used herein to describe a material having one or more properties sufficiently well established to be used for calibration of an apparatus or assay, for the assessment of a measurement methodology, and for the verification of one or more measurements in other materials. Such properties may be prion protein concentration, infectious units of prions, genetic identity, background protein concentration, and the like. For example, a standardized prion preparation with an established concentration of prion can be used as a reference material for an assay to determine prion concentration in a sample potentially infected with prions, or to determine that a particular assay conforms to a desired detection level.

The term "sensitivity" as used herein refers to the relative strength of recognition of a protein by a binding partner, e.g. an antibody or antisense molecule. The recognition of the prion protein must be significantly greater than the recognition of background proteins, and preferably the strength of recognition of the prion protein by the binding partner is at least 10 times, more preferably at least 100 times greater, and even more preferably at least 500 times greater than recognition of background proteins.

The term "selectivity" as used herein refers to the preferential binding of a binding partner for an epitope on a prion protein. Preferably, a prion protein binding partner is at least 10 times, more preferably 100 times, and even more preferably 1000 times more likely to bind to an epitope on a prion protein than to any epitope on a background protein.

The term "infectious unit" as used herein refers to an amount of prions which is capable of causing a prion-mediated infectious disease in an animal upon exposure to this amount. Exposure to an amount of prions below one infectious unit will generally not result in infectivity of those prions, and thus amounts below one infectious unit may not be detected in a prion in vivo bioassay, i.e., only a hypersensitive bioassay will detect such. Generally, a single infectious unit is approximately $10^5$ PrP molecules, although the number may vary with the virulence of the prion strain.

The term "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the PrP$^C$ form and the disease related form referred as the PrP$^{Sc}$. Although a prion protein or the PrP$^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The terms "PrP protein", "PrP" and like are used interchangeably herein and shall mean both the infectious particle form PrP$^{Sc}$ known to cause diseases (spongiform encephalopathies) in humans and animals and the noninfectious form PrP$^C$ which, under appropriate conditions is converted to the infectious PrP$^{Sc}$ form.

The terms "prion", "prion protein" and "PrP$^{Sc}$ protein" and the like are used interchangeably herein to refer to the infectious PrP$^{Sc}$ form of PrP, and is a contraction of the words "protein" and "infection." Particles are comprised largely, if not exclusively, of PrP$^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a PrP protein. Some commonly known PrP sequences are described in Gabriel et al., Proc. Natl. Acad. Sci. USA 89:9097–9101 (1992), and U.S. Pat. Nos. 5,565, 186; 5,763,740; 5,792,901; and W097/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a PrP$^C$ (non-disease) or PrP$^{Sc}$ (disease) form.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 of U.S. Pat. No. 5,565,186 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals, but may include codons and codon sequences associated with genetic prion diseases such as CJD and codons and sequences not associated with any native PrP gene but which, when inserted into an animal, render the animal susceptible to infection with prions which would normally only infect a genetically diverse animal.

The terms "chimeric gene," "chimeric PrP gene", "chimeric prion protein gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C- terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Antibodies for assays of the invention may be immunoreactive or immunospecific for and therefore specifically and selectively bind to a protein of interest e.g., an A4β amyloid protein or a PrP protein. Antibodies which are immunoreactive and immunospecific for both the native non-disease form and the treated disease form but not for the untreated disease form (e.g., for both native PrP$^C$ and treated PrP$^{Sc}$ but not native PrP$^{Sc}$) may be used because the sample is treated to remove, i.e., hydrolyze PrP$^C$. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Ser. No. 08/713,939. Antibodies disclosed in the PCT application which bind PrP$^{Sc}$ can be used to carry out the basic assay of the present invention when the sample has been treated with dispase sufficiently to hydrolyze all or substantially all of the PrP$^C$ present in the sample. Another useful antibody for binding to PrP$^C$ is the monoclonal antibody 263K 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No. 4,806,627 issued Feb. 21, 1989—incorporated by reference to disclose antibodies which selectively bind PrP$^C$. The term "antibody" encompasses all types of antibodies, e.g. polyclonal, monoclonal, and those produced by the phage display methodology. Particularly preferred antibodies of the invention are antibodies which have a relatively high degree of affinity for both native PrP$^C$ and treated PrP$^{Sc}$ but a relatively low degree of or substantially no binding affinity for PrP$^{Sc}$. More specifically, antibodies of the invention preferably have four times or more, more preferably fifteen times or more, and still more preferably 30 times or more binding affinity for both native PrP$^C$ and denatured PrP$^{Sc}$ as compared with the binding affinity for native PrP$^{Sc}$.

"Purified antibody" refers to that which is sufficiently free of other proteins, carbohydrates, and lipids with which it is naturally associated. Such an antibody "preferentially binds" to a denatured disease conformation of a protein such as the denatured PrP$^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native PrP$^C$ and for denatured forms of PrP$^C$ and PrP$^{Sc}$ or, alternatively, for native or untreated PrP$^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., denatured PrP$^{Sc}$ or denatured A4β protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as PrP$^{Sc}$ so that by adjusting binding conditions the antibody binds almost exclusively to an epitope site or fragments of a desired protein such as an epitope fragment exposed by denaturing of PrP$^{Sc}$ and not exposed on native PrP$^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/ diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene of the present invention or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP gene", "disrupted PrP gene", "ablated PrP gene" and the like are used interchangeably herein to mean an endogenous PrP gene which has been altered (e.g., add and/or remove nucleotides) in a manner so as to render the gene inoperative. Examples of non-functional PrP genes and methods of making such are disclosed in Büeler, H., et al "Normal development of mice lacking the neuronal cell-surface PrP protein" Nature 356:577–582 (1992) which is incorporated herein by reference. Both alleles of the genes are preferably disrupted.

The terms "hybrid animal", "transgenic hybrid animal" and the like are used interchangeably herein to mean an animal obtained from the cross-breeding of a first animal having an ablated endogenous PrP gene with a second animal which includes either (1) a chimeric gene or artificial PrP gene or (2) a PrP gene from a genetically diverse animal. For example a hybrid mouse is obtained by cross-breeding a mouse with an ablated mouse PrP gene with a mouse containing (1) bovine PrP genes (which may be present in high copy numbers) alone or with (2) chimeric PrP genes. The term hybrid includes any offspring of a hybrid including inbred offspring of two hybrids provided the resulting offspring is susceptible to infection with prions with normal infect only a genetically diverse species and the symptoms of the infection are observable in about 350 days or less, preferably 250 or less.

The terms "susceptible to infection" and "susceptible to infection by prions" and the like are used interchangeably herein to describe a transgenic or hybrid test animal of the invention which develops a prion disease if inoculated with prions which would normally only infect a genetically diverse test animal. The terms are used to describe a transgenic or hybrid animal of the invention such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection). If an animal is susceptible to infection with a particular prion that animal, if inoculated with the prion, will show symptoms of prion disease infection in about 350, preferably 250 days or less.

The term "incubation time" shall mean the time from inoculation of an animal with a prion until the time when the animal first develops detectable symptoms of disease resulting from the infection. A reduced incubation time is one year or less, preferably about 200 days±50 days or less, more preferably about 50 days±20 days or less.

The terms "standardized prion preparation", "prion preparation", "preparation" and the like are used interchangeably herein to describe a composition containing prions which composition is obtained from brain tissue of mammals which contain substantially the same genetic material as relates to prions, e.g., brain tissue from a set of mammals which exhibit signs of prion disease which mammals (1) include a transgene of the invention; (2) have an ablated endogenous prion protein gene; (3) have a prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease due to their genetically modified make up, e.g., species specific prion protein genes.

The term "endogenous prion protein concentration" and "endogenous prion concentration" as used herein refers to the concentration of the endogenous prion protein in the brain homogenate of the standard. For example, the endogenous prion protein of a standard generated using prion ablated host animals should preferably be undetectable. In another example, the endogenous prion protein of a standard generated using brain homogenate of a normal genetically diverse animal should only have $PrP^{C}$ present, and these levels should be within the physiologically normal range of that animal, e.g. a standard using normal bovine brain should have an endogenous prion concentration within the range of a normal bovine brain.

The term "exogenous prion protein concentration" as used herein refers to the concentration of prions, e.g. prions of a genetically diverse species, produced in a host mammal. The term refers to both $PrP^{C}$ and $PrP^{Sc}$, or a combination of the two depending on the context. The exogenous prion protein concentration refers to the level of exogenous prions in the brain homogenate of host animals infected with prions that normally infect a genetically diverse species. Alternatively, exogenous prion protein concentration can refer to the concentration of isolated prion protein introduced into the standard.

The term "background protein concentration" as used herein refers to levels of any background protein, i.e. any protein other than prions present in the brain preparation used to generate the standard.

The term "assay value" as used herein refers to the levels of prion detected in a sample, a standard, or a portion of a standard using an assay designed to detect prion concentration or infectivity.

The term "true value" as used herein refers to the level of prion protein present in a sample that is detectable using reliable techniques known in the art for determining protein levels.

The term "correction value" as used herein refers to the numerical adjustment needed to convert the prion assay value to the true value. The correction value may be additive, multiplicative, or exponential, depending on the assay.

Abbreviations used herein include:

CNS for central nervous system;

BSE for bovine spongiform encephalopathy;

CJD for Creutzfeldt-Jacob Disease;

FFI for fatal familial insomnia;

GdnHCI for Guanidine hydrochloride;

GSS for Gerstamnn-Strassler-Scheinker Disease;

Hu for human;

HuPrP for human prion protein;

Mo for mouse;

MoPrP for mouse prion protein;

SHa for a Syrian hamster;

SHaPrP for a Syrian hamster prion protein;

Tg for transgenic;

Tg(SHaPrP) for a transgenic mouse containing a PrP gene of a Syrian hamster;

Tg(BovPrP) for transgenic mice containing the complete human PrP gene;

Tg(ShePrP) for transgenic mice containing the complete sheep PrP gene;

Tg(BovPrP) for transgenic mice containing the complete cow PrP gene;

$PrP^{Sc}$ for the scrapie isoform of the prion protein;

$PrP^{C}$ for the cellular contained common, normal isoform of the prion protein;

PrP 27–30 or $PrP^{Sc}$ 27–30 for the treatment or protease resistant form of $PrP^{Sc}$;

$MoPrP^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the chimeric MHu2M gene;

$MHu2MPrP^{Sc}$ for the scrapie isoform of the chimeric human/mouse PrP gene;

$PrP^{CJD}$ for the CJD isoform of a PrP protein;

$Prnp^{0/0}$ for ablation of both alleles of an endogenous prion protein gene, e.g., the MoPrP gene;

$Tg(SHaPrP^{+/0})81/Prnp^{0/0}$ for a particular line (81) of transgenic mice expressing SHaPrP, +/0 indicates heterozygous;

$Tg(HuPrP)/Prnp^{0/0}$ for a hybrid mouse obtained by crossing a mouse with a human prion protein gene (HuPrP with a mouse with both alleles of the endogenous prion protein gene disrupted;

$Tg(MHu2M)/Prnp^{0/0}$ for a hybrid mouse obtained by crossing a mouse with a chimeric prion protein gene (MHu2M) with a mouse with both alleles of the endogenous prion protein gene disrupted;

FVB for a standard inbred strain of mice often used in the production of transgenic mice since eggs of FVB mice are relatively large and tolerate microinjection of exogenous DNA relatively well.

STANDARDIZED PREPARATIONS—IN GENERAL

Standardized preparations are generally characterized by containing a known amount of a disease related conformation of a protein. The protein may be any protein with two or more three dimensional conformations and is preferably a composition containing a known amount of a PrP protein in its disease conformation, i.e. a known amount of $PrP^{Sc}$. The amount of $PrP^{Sc}$ may be an amount in terms of infectious units of $PrP^{Sc}$, concentration of $PrP^{Sc}$, or number of molecules of $PrP^{Sc}$ present in a unit volume of the sample. An array of preparations containing different amounts of $PrP^{Sc}$ and/or different strains would provide a useful kit for bioassays or immunoassays.

A standardized prion preparation of the invention is comprised of: (1) prions obtained from a plurality of different sources, e.g., a plurality of genetically identical transgenic mice and (2) a carrier which is not the brain tissue of the animals normally infected by the prions. The prions are of a known strain, present in a known amount and infect and cause disease in a known species of animal. The prions are preferably obtained from the brains of 10 or more transgenic mice which have been genetically manipulated so that they are infectable with a specific strain of prions which generally only infects a human, cow or sheep.

Standardization of assays to detect prion proteins requires a demonstration of precision and accuracy in the measurement of prion protein in a sample. Precision requires that prion concentrations obtained in replicate assays should be in good agreement within a selected standard of error. Preferably, the standard of error is $10^{0.2}$ at $ID_{50}$ units/ml, where $ID_{50}$ unit is defined as the infectious dose at which 50% of the test animals develop prion disease. Precision can be obtained by quality and consistency of reagents and protocols used in the assays. Accuracy requires that the concentration obtained in the assay should either reflect the true concentration of the prion protein in the sample, or that the true concentration can be reproducibly determined by altering the obtained value by a constant factor. Accuracy is best optimized by careful and consistent methodology, quality of technical determination of protein concentrations, and a minimization of error.

In addition, if different methods are used to detect prion protein, standardization requires a harmonization of the data obtained using the different methods. Different protocols to determine prion protein concentrations may vary with respect to a number of factors, for example the storage of the sample, the preparation of the sample prior to visualization of the protein, the chemicals used in the processing of the sample, and the like. Many potential changes in prion protein levels from obtaining, storing or preparing samples for prion assays are method-dependent. Harmonization of data can be achieved by using suitable standard reference materials. To be suitable for harmonization, reference standards should have the same immunochemical behavior as the samples to be analyzed in all methods. In addition, it is crucial that the standards be consistent, i.e. the prion concentration does not noticeably vary in different samples of the standard, and reproducible, i.e. the values obtained using different samples of the standard do not vary outside a standard of error. The reference standard may have a number of different physical forms, and may be lyophilized, liquid-stabilized, frozen, etc.

Standardized Prion Preparation

Prion standards are produced for use in assays so as to determine the specificity, sensitivity and/or reliability of the assay. Standards are produced using standardized prion preparations from any host animal, although preferably the preparations are obtained from a host animal which has brain material containing prions of a test animal. For example, a Tg mouse containing a human prion protein gene can produce human prions and the brain of such a mouse can be used to create a standardized human prion preparation. Further, in that the preparation is to be a "standard" it is preferably obtained from a battery (e.g., 100, 500, 1,000, or more animals) of substantially identical animals. For example, 100 mice all containing a very high copy number of human PrP genes (all polymorphisms and mutations) would spontaneously develop disease and the brain tissue from each could be combined to make a useful standardized human prion preparation. The preparation is potentially infinite in size because substantially identical preparations can be produced at any time by following an established protocol.

Standardized prion preparations can be produced using any of the modified host mammals of the present invention. For example, standardized prion preparations could be produced using mice, rats, hamsters, or guinea pigs which are genetically modified per the present invention so that they are susceptible to infection with prions which prions would generally only infect genetically diverse species such as a human, cow, sheep or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals.

Once an appropriate type of host is chosen, such as a mouse, the next step is to choose the appropriate type of genetic manipulation to be utilized to produce a standardized prion formulation. For example, the mice may be mice which are genetically modified by the insertion of a chimeric gene of the invention. Within this group the mice might be modified by including high copy numbers of the chimeric gene and/or by the inclusion of multiple promoters in order to increase the level of expression of the chimeric gene. Alternatively, hybrid mice of the invention could be used wherein mice which have the endogenous PrP gene ablated are crossed with mice which have a human PrP gene inserted into their genome. There are, of course, various subcategories of such hybrid mice. For example, the human PrP gene may be inserted in a high copy number and/or used with multiple promoters to enhance expression. In yet another alternative the mice could be produced by inserting multiple different PrP genes into the genome so as to create mice which are susceptible to infection with a variety of different prions, i.e., which generally infect two or more types of test animals. For example, a mouse could be created which included a chimeric gene including part of the sequence of a human, a separate chimeric gene which included part of the sequence of a cow and still another chimeric gene which included part of the sequence of a sheep. If all three different types of chimeric genes were inserted into the genome of the mouse the mouse would be susceptible to infection with prions which generally only infect a human, cow and sheep.

After choosing the appropriate mammal (e.g., a mouse) and the appropriate mode of genetic modification (e.g., inserting a chimeric PrP gene) the next step is to produce a large number of such mammals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g., within ±30 days of each other.

Once a large group e.g., 50 or more, more preferably 100 or more, still more preferably 500 or more of such mice are produced. The next step is to inoculate the mice with prions which generally only infect a genetically diverse mammal e.g., prions from a human, sheep, cow or horse. The amounts given to different groups of mammals could be varied. After inoculating the mammals with the prions the mammals are observed until the mammals exhibit symptoms of prion infection, e.g., clinical signs of CNS dysfunction. After exhibiting the symptoms of prion infection the brain or at least a portion of the brain tissue of each of the mammals is extracted. The extracted brain tissue is homogenized which provides the standardized prion preparation.

As an alternative to inoculating the group of transgenic mice with prions from a genetically diverse animal it is possible to produce mice which spontaneously develop prion related diseases. This can be done, for example, by including extremely high copy numbers of a human PrP gene into a mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce a standardized prion preparation.

The standardized prion preparations of the invention can be used directly or can be diluted and titered in a manner so as to provide for a variety of different positive controls. More specifically, various known amounts of such standardized preparation can be used to inoculate a first set of transgenic control mice. A second set of substantially identical mice are inoculated with a material to be tested, i.e., a material which may contain prions. A third group of substantially identical mice are not injected with any material. The three groups are then observed. The third group, should, of course, not become ill in that the mice are not injected with any material. If such mice do become ill the assay is not accurate probably due to the result of producing mice which spontaneously develop disease. If the first group, injected with a standardized preparation, do not become ill the assay is also inaccurate probably because the mice have not been correctly created so as to become ill when inoculated with prions which generally only infect a genetically diverse mammal. However, if the first group does become ill and the third group does not become ill the assay can be presumed to be accurate. Thus, if the second group does not become ill the test material does not contain prions and if the second group does become ill the test material does contain prions.

By using standardized prion preparations of the invention it is possible to create extremely dilute compositions containing the prions. For example, a composition containing one part per million or less or even one part per billion or less can be created. Such a composition can be used to test the sensitivity of the transgenic mice of the invention in detecting the presence of prions in the sample.

Prion preparations of the present invention are desirable in that they will include a constant amount of prions and are extracted from an isogeneic background. Accordingly, contaminates in the preparations will be constant and controllable. Standardized prion preparations of the invention will be useful in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations of the invention will be valuable in validating purification protocols where preparations are spiked and reductions in teeter measured for a particular process.

TRANSGENIC ANIMALS AS PRION SOURCE

Prion protein standards of the invention are useful as standards of infectivity in an in vivo assay for prion infection. The host animals used in these assays are genetically altered to be susceptible to prions which normally only infect a species genetically diverse from the host animal. The DNA sequence of the human, sheep and cow PrP genes have been determined allowing, in each case, the prediction of the complete amino acid sequence of their respective prion proteins. The normal amino acid sequence which occurs in the vast majority of individuals is referred to as the wild-type PrP sequence. This wild-type sequence is subject to certain characteristic polymorphic variations. In the case of human PrP, two polymorphic amino acids occur at residues 129 (Met/Val) and 219 (Glu/Lys). Sheep PrP has two amino acid polymorphisms at residues 171 and 136, while bovine PrP has either five or six repeats of an eight amino acid motif sequence in the amino terminal region of the mature prion protein. While none of these polymorphisms are of themselves pathogenic, they appear to influence prion diseases. Distinct from these normal variations of the wild-type prion proteins, certain mutations of the human PrP gene which alter either specific amino acid residues of PrP or the number of octarepeats have been identified which segregate with inherited human prion diseases. These polymorphisms and mutations are summarized in the following table:

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 | Codon 136 | |
| 5 octarepeat insert | Glu/Lys | Ala/Val | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

Mutations and polymorphisms in the genes of genetically diverse animals can be introduced to host animals to create the standards of the invention. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmamn et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). Further PrP sequences and differences between sequences and known mutations are disclosed in U.S. Pat. No. 5,792,901 issued Aug. 11, 1998. These publications are all incorporated herein by reference to disclose and describe the PrP gene and PrP amino acid sequences that may be used in the generation of the standards of the invention.

In one preferred embodiment of the invention, the test animal used in the assay is Tg(HuPrP)Prnp$^{0/0}$, and the prion protein standard produced for this assay is generated using this strain of mouse. The HuPrP construct may vary with respect to known polymorphisms as well as known pathogenic mutations. Thus, when the genetic material is expressed, the resulting protein will be HuPrP. After the human PrP transgene is produced, it can be microinjected into a mouse egg using known technology as described within Scott et al. *Cell* 59:847–857 (1989) and Scott et al., *Protein Sci.* 1:986–997 (1992) and see also WO91/19810 published Dec. 22, 1991 as well as other publications relating to the production of transgenic mice cited therein and known to those skilled in the art.

In another preferred embodiment, the test animal is a mouse with an ablated endogenous PrP gene and an exogenous bovine PrP gene, Tg(BovPrP)/Prnp$^{0/0}$. A construct containing the full-length bovine PrP gene is stably introduced to the genome of a PrP$^{0/0}$ mouse by microinjection of the construct into a PrP$^{0/0}$ egg. The injected mouse egg is then implanted into a mouse using known procedures. Multiple eggs can be implanted into a single mouse and known procedures can be used to determine whether the resulting offspring are transgenic mice which include the transgene within their genome.

Quality control of prion protein standards

Once the standard of the invention is prepared, it needs to undergo a series of tests and controls to check the established properties of the standard sufficiently well established to allow use of the standard. The properties should be determined not only for the new batch, but also for consistency between different aliquots of the batch. For a prion protein standard, properties such as prion concentration, antigenicity, background elements, and the like.

Moreover, the standard needs to be stored in such a manner that it preserves its initial chemical, physical and biological properties over time. Thus, the standard should be stored in a manner that minimizes biodegradation, chemical transformations, change of the oxidative state of portions of the sample, interaction with the storage container, and other reactions that may take place during storage. Tests to evaluate possible changes occurring during storage can be performed by analyzing the materials at different times.

The levels of prion in a sample can also be maintained by "spiking" the standard with the appropriate isolated prion protein, i.e. adding purified prion protein in order to maintain a desired level of prion protein in a sample. The added protein may be either PrP$^{C}$ or PrP$^{Sc}$ as necessary to achieve the desired parameters of the standard, and it may be either the whole protein or the segment that is infective (e.g. for the in vivo infectivity assay) or the fragment that is antigenic (e.g. for an immunoassay). These spiked materials may be very useful in enhancing laboratory performance, especially for analytical methods for specific types of materials such as prions, which may be at extremely low concentrations in the initial stages of infection.

Spiked in vivo material as prion standard

In another embodiment, normal or diseased tissue from a mammal is spiked with prions that normally infect that species. The isolated prions are produced from transgenic mice that are susceptible to infection by prions from the genetically diverse species. For instance, normal bovine brain can be spiked with prions harvested from Tg(BovPrP)/PrP$^{0/0}$ mouse which correspond to prions that naturally infect cows. In another example, the brain homogenate is prepared from the brain of a cow suffering from BSE. The initial inocula used to infect the Tg(BovPrP)/PrP$^{0/0}$ preferably comes from a cow genetically similar to the cow brain being used as the preparation material for the standard. This embodiment of the invention may be preferable for an assay in which the background (e.g. proteins, etc.) of cow brain is extremely important, but a standardized concentration of prion and/or infectivity level is needed in order to standardize a procedure, test a reagent, and the like.

Standards to test efficacy of reagents for assays

The standards of the invention provide a practical means for uniform testing of antibodies and other reagents used in immunoassays under defined conditions. A variety of different types of assays of the invention may be used with one or more different agents that recognize prions, such as antibodies. These antibodies can be tested for immunoreactivity, specificity for a particular conformation, and /or cross-reactivity with prions from different species using the standards of the invention. For example, each new antibody, whether it is a new monoclonal antibody to a different epitope, a new hybridoma producing an antibody predicted to recognize a known epitope, or a new batch of polyclonal antibodies, can be evaluated for immunoreactivity using a prion standard preparation. The availability of a standard preparation of prion proteins would permit producers of reagents used in the assays to establish an internal quality control program. In addition, having the standard used to determine the specificity and reproducibility of the reagents available to those performing the assay would allow laboratories to conduct performance testing of all assays using standardized reagents.

Methods of generating antibodies are generally known to those skilled in the art. In that the disease form is often in a tighter configuration than the non-disease form, with less epitopes exposed, one can readily generate antibodies which bind only to the non-disease form of the protein or the treated disease form. For example, antibodies detecting treated forms of PrP$^{Sc}$ protein and PrP$^{C}$ protein may be generated by immunizing rabbits or mice with a-helical conformations of recombinant PrP, native PrP$^{C}$ from animal brains, synthetic peptides in $\alpha$-helical or random coil conformations, or against denatured PrP$^{Sc}$ or PrP 27–30. Only antibodies with affinity at least 4 fold higher for PrP$^{C}$ (or denatured conformation of PrP$^{Sc}$ of the same species) as compared to their affinity for PrP$^{Sc}$ should be selected. The method of antibody generation, purification, labeling and detection may vary. An antibody which can be used in the invention is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference. The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies which bind to either $PrP^C$ or $PrP^{Sc}$ are disclosed in W097/10505, published Mar. 20, 1997. Any antibody binding to $PrP^C$ and not to $PrP^{Sc}$ can be used, and those skilled in the art can generate such using known procedures, e.g., see methods of producing page display antibody libraries in U.S. Pat. No. 5,223,409. Polyclonal anti-PrP antibodies have though been raised in rabbits following immunization with large amounts of formic acid or SDS-denatured SHaPrP 27–30 [Bendheim, Barry et al. (1984) *Nature* 310:418–421]; Bode, Pocchiari et al. (1985) *J Gen Virol* 66:2471–2478; Safar, Ceroni et al. (1990) *Neurology* 40:513–517). Similarly, a handful of anti-PrP monoclonal antibodies against PrP 27–30 have been produced in mice [Barry and Prusiner (1986) *J Infect Dis* 154:518–521; Kascsak, Rubenstein et al. (1987) *J Virol* 61:3688–3693]. These antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) *Proc Natl Acad Sci USA* 90:3182–3186].

Antibodies secreted from a single hybridoma can be tested to ensure that they retain the desired level of detection, since the standards of the invention provide a sample with reproducible antigenicity. Accordingly, a hybridoma can be monitored for stability of production and, if necessary, a new hybridoma expressing the antibody of choice can be isolated and tested for a specific level of binding to the PrP gene product. Testing the antibodies against a standard and a control (e.g. the transgenic animals used to produce the standard that have not been infected) will also allow standardization of the cross-reactivity of the antibodies, which is especially useful in ensuring that antibodies such as R1 bind to both conformations of the prion protein, or that an antibody such as 3F4 binds preferentially to one native conformation, but binds well to both conformations upon denaturation.

Multiprion Standards

In one embodiment of the invention, a standard may be used that provides a reference material for multiple strains of prion at one time. The different prions in the standard may be variants from a single species, or may contain prions from multiple species. The different prions in the standard may be interspersed in the sample such that cross-reactivity and/or specificity is determined primarily through the intensity of the signal produced, or by a double labeling procedure. For instance, if a multiprion standard contains different samples of prions that will infect sheep, cows, and goats, with such prions being in roughly equal concentration, an antibody that recognizes a conserved epitope on all three prions will result in a signal three times as strong as an antibody that only recognizes an epitope specific to a sheep prion. Alternatively, the cross-reactivity of an antibody with multiple species can be determined by also subjecting the tissue to an antibody that is specific to one of the prions in the multiprion standard.

In a preferred embodiment, a multiprion standard is provided in which multiple samples of prion of different variants and/or species are discretely distributed in a single standard, allowing the identification of the particular sample that reacts with an agent. One example of such a standard is a checkerboard tissue block, which can serve as a multipurpose control for slides, the evaluation of new reagents, specificity of assays, etc. The physical structure of such a standard is described in Battifora and Matha, *Lab Invest.* 68:722–24 (1990) and in Petrosyan and Press, *Lab Invest* 77:541–542 (1997), both of which are incorporated herein by reference.

EXAMPLES

The following examples are put forth so as to provide those of ordinary skill in the art with a complete disclosure and description of how to make and use standards of the present invention, and are not intended to limit the scope of what the inventors regard as their invention, nor are they intended to represent or imply that the experiments below are all of or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Creation of a Tg(BovPrP) Strain for Standard Preparation

When using a standard to assess the presence and infectivity of prion protein within a bovine sample, it is desirable to have a standard having a known relatively constant amount of bovine prions. It is also desirable to have a standard with a PrP gene as genetically similar to the bovine test material as possible. To this end, the prion standard for testing bovine material for prion proteins can be produced using a transgenic mouse with its endogenous PrP gene replaced by an exogenous bovine PrP gene.

Transgenic mice having an endogenous Tg(BovPrP)/ $PrP^{0/0}$ mice are created and propagated as disclosed in U.S. Pat. No. 5,792,901, which is incorporated herein by reference. The bovine PrP gene is introduced to produce Tg(BovPrP)/$PrP^{0/0}$ that are susceptible to bovine prions from cattle with BSE. The Tg(BovPrP)/$PrP^{0/0}$ mice produce prions capable of infecting cows within their brain tissue. The brains of these mice or portions of the brain tissue of these animals are extracted and homogenized to produce a standardized prion preparation for use as a prion protein standard. A 10% [w/v] homogenate of infected brain tissue from an infected Tg(BovPrP)/$PrP^{0/0}$ mouse is prepared in phosphate buffered saline lacking calcium and magnesium ions. The tissue is initially dissociated using a sterile disposable homogenizer, and this suspension was subjected to repeated extrusion through an 18 gauge syringe needle followed by a 22 gauge needle. Samples to be used as standards are assayed for desired properties, e.g. $PrP^{Sc}$ concentration and overall prion concentration, are diluted 1 0-fold, and stored.

Example 2

Creation of a Tg(HuPrP) Strain for Standard Preparation

Transgenic mice having an endogenous PrP gene and an exogenously introduced human PrP gene can be used to produce a standard for detecting prions in human material. The human transgene Tg(HuPrP) introduced to the transgenic mice can encode any human prion strain, including known non-pathogenic polymorphisms, germline PrP mutations, known sporadic PrP mutations, etc. In this manner the PrP gene of the standard may be designed to be genetically similar to the human test material. Thus, the use of the term Tg(HuPrP) herein includes human transgenes having different polymorphisms and/or mutations.

Human inocula are derived from frozen brain tissues of patients in which the clinical diagnosis of CJD, GSS, or FFI had been confirmed by histopathological examination of brain tissues and, in most cases, by prion protein analysis. In some cases, the PrP gene was amplified by PCR of DNA isolated from patient blood and the PrP sequence determined by DNA sequence analysis. Human brain specimens are collected from patients dying of sporadic, inherited or infectious prion disease. A 10% [w/v] homogenate of brain tissue from a patient diagnosed with CJD, GSS, or FFI is prepared in phosphate buffered saline lacking calcium and magnesium ions. The tissue is initially dissociated using a sterile disposable homogenizer, and this suspension is subjected to repeated extrusion through an 18 gauge syringe needle followed by a 22 gauge needle. Samples for inoculation into test animals are diluted 10-fold.

Tg(HuPrP)/PrP$^{0/0}$ mice are created and propagated as disclosed in U.S. Pat. No. 5,792,901, which is incorporated herein by reference. These mice are inoculated intracerebrally with 30 μl of infected brain extract using a 27 gauge needle inserted into the right parietal lobe. The preparation of inocula and criteria for diagnosis of scrapie are as described above in Example 1. Homogenate of either the brain of a single infected animal or a plurality of animals infected with the same inocula is then used to inoculate a larger number of Tg(HuPrP)/PrP$^{0/0}$ mice, which are then followed for signs of infectivity. Depending on the level of prion protein desired in the standard, animals can be killed at a specific time following innoculation and/or when they exhibit a specific physiological response to infection, e.g. a certain degree of ataxia. These brain samples are pooled, and a new batch of Tg(HuPrP)/PrP$^{0/0}$ mice inoculated with the homogenate. This continues, with a new batch of mice used for the production of the standard being inoculated with inocula from a preceding generation, and most preferably from the infected mice directly preceding the new generation. Alternatively, several generations of mice can be infected with the inocula of a single earlier generation. This procedure allows the standardization of the prion concentration of the standard while diminishing the background due to genetic variation of the prion preparation.

Total protein concentrations in brain homogenates are determined by bicinchoninic acid assay. Immuno dot blots for the determination of the relative levels of PrP expression in Tg mouse brains are performed as previously described (Scott et al., 1993). Samples for Western blot analyses are prepared by digesting brain homogenates with 20 μg proteinase K for 60 min at 37° C. Western blots are performed as described previously in Barry, R. A., et al., "Monoclonal antibodies to the cellular and scrapie prion proteins," J. Infect. Dis., 154:518–521 (1986); Towbin, H., et al., "Electrophoretic transfer of proteins from polyacrylamide gels to nitrocellulose sheets: Procedure and some applications," Proc. Natl. Acad. Sci. USA 76:4350–4354 (1979), except that an enhanced chemiluminescent (ECL) detection method (Amersham, Arlington Heights, Ill.) was used. The lot is exposed to X-ray film α-PrP R073 rabbit antiserum is used at a final dilution of 1:5000.

Example 3

Production and use of a Syrian Hamster Prion Standard

For the development of a standard for calibration of an assay, recombinant Syrian hamster prion proteins of sequence 90–231 were refolded into α-helical or β-sheet conformations as described [Mehlhorn, Groth et al. (1996) Biochemistry 35:5528–5537]. PCR (Perkin-Elmer) was used to amplify the DNA corresponding to different portions of the Syrian hamster prion protein in order to ligate it into E. coli secretion vectors. Several 5' oligonucleotide primers were synthesized with an Mlu I restriction site within the C-terminal coding sequence of the STII signal peptide [Lee, Moseley et al. (1983) Infect Immun 42:264–268; Picken, Mazaitis et al. (1983) Infect Immun 42:269–275] and the initial amino acids of the appropriate PrP sequence. One 3' oligonucleotide primer matching the 3' end of PrP, a stop codon and a Bam HI restriction site was used with each of the 5' oligonucleotides. The PCR amplified products were purified, ligated into the vectors previously digested with MluI/Bam HI and transformed into DH5a. Clones containing the PrP insert were sequenced and transformed into the protease deficient expression strain 27C7 (ATCC# 55244).

Large scale expression was carried out as described previously for other proteins using a different medium [Carter, Kelley et al. (1992) Biotechnology 10: 163–167]; 500 mL of an overnight culture grown in LB medium supplemented with ampicillin was inoculated into 7 L of fermentation medium in an aerated 10 L fermentor (Braun, model E 10). Cells were grown at 37° C. at a high agitation rate, and expression was induced by phosphate starvation. After 4 h, a 50% glucose solution was added at a rate of 1 mL/min; glucose levels were monitored using a glucose dipstick (Diastix, Miles Inc.). A pH of 7.4 was maintained throughout the run by the automated addition of 10% $H_2SO_4$ or 24% $NH_4OH$. The final volume was 10 L in which an OD600 of ≧100 was achieved after 36 h. The E. coli was harvested by centrifugation at 10,000 x g for 30 min and the resulting paste was stored at −20° C.

For purification, 100 g of E coli paste was resuspended in 1 L of 25 mM Tris.HCl, pH 8.0, 5 mM EDTA (buffer A). This was centrifuged at 10,000 x g for 20 min, and the supernatant containing soluble periplasmic proteins was discarded. The pellet was resuspended in 1 L of buffer A, passed through a cell disrupter twice (Microfluidics International, model MF 110), and centrifuged at 30,000 x g for 1 h, after which the supernatant was discarded and the pellet was washed once in buffer A and centrifuged again at 30,000 x g for 1 h. At this stage the pellet could be stored at −20° C. prior to further separation. It was subsequently solubilized in 8M Gdn.HCl/25 mM Tris-HCl, pH 8.0/100 mM DTT (buffer B) and centrifuged at 14,000 x g for 20 min to remove the remaining insoluble matter. Aliquots of 6 mL of the supernatant containing ~200 mg total protein were separated by size exclusion chromatography (SEC) using a 26 mm x 60 cm HiLoad Superdex 200 column (Pharmacia), eluting with 6M Gdn.HCl/12.5 mM Tris-HCl, pH 8.0/5mM DTT/1 mM EDTA (buffer C) at a flow rate of 2 mL/min. Fractions enriched for the recombinant prion protein as identified by SDS-PAGE were pooled and further purified by reversed phase high performance liquid chromatography (RP-HPLC) employing a 25 mm x 25 cm C-4 column (Vydac); Buffer 1: $H_2O/0.1\%$ TFA, Buffer 2: acetonitrile/

0.09% TFA, flow rate 5 mL/min. The recombinant protein rPrP was found in fractions containing 40% acetonitrile. If the SEC eluate was stored at 4° C. for several days prior to RP-HPLC, the recombinant protein was eluted in earlier fractions containing only 35% acetonitrile.

Samples of the reduced protein and the refolded oxidized form were concentrated using a Centricon column (Amicon) with a molecular weight cut-off of 10,000 Da. The buffer for the reduced protein was 10 mM MES, pH 6.5 whereas the oxidized form was concentrated in the refolding buffer described above. The conformations of refolded oxidized and reduced forms of SHaPrP90–231 protein were determined by circular dichroism (CD) spectroscopy (FIG. 1).

Purified recombinant SHaPrP90–23 1, refolded into α-helical or β-sheet conformation, was diluted into 5% (w/v) brain homogenate obtained from PrP$^{0/0}$ mouse and containing no prion protein. The brain homogenate was made by three 30 sec bursts in PowerGen homogenizer equipped with plastic disposable probe in TBS, pH 7.4 containing protease inhibitors cocktail (1 mM PMSF, 2 μg/ml of Aprotinin, and 2 μg/ml of Leupeptin) and spun at 5° C. for 5 min at 500 G in a desktop centrifuge. The resulting supernatant was diluted 1:1 in TBS with final 4% (w/v) Sarcosyl and homogenized again by three 30 sec bursts in a PowerGen homogenizer. Next, the homogenate was spiked with different dilutions of recombinant SHaPrP90–23 1 in α-helical or β-sheet conformations.

In a typical competitive assay, the analyte PrP in different conformations is preincubated with europium labeled 3F4 IgG and then transferred to the polystyrene plate coated with recombinant ShaPrP90–23 1 in SDS-denatured state. The results for analyte SHaPrP90–23 1 in α-helical and denatured state indicate marked difference in both available binding sites and affinity of europium-labeled 3F4 IgG with different conformations of prion protein.

In a direct assay, each sample to be tested and the standard were divided into two aliquots: (I) untreated and designated native; (2) mixed with final 4M Gdn HCl and heated for 5 min at 100° C. and designated denatured. Both samples and standard were diluted 20-fold by $H_2O$ and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (w/v) of Tween® 20 and incubated with europium-labeled antibodies listed above. The plates were developed after an additional 7 washing steps in enhancement solution provided by the europium label supplier (Wallac Inc., Turku, Finland) and signal counted on DELFIA 1234 Fluorometer (Wallac Inc., Turku, Finland).

Example 4

Creation of a Human Prion Protein Standard and use in Calibration of Assays

Tg(HuPrP)/$PrP^{0/0}$ mice are created and propagated as described in Example 2. These mice are inoculated intracerebrally with 30 μl of infected brain extract using a 27 gauge needle inserted into the right parietal lobe. The inocula of the mice may be from any human prion preparation, with examples of such inocula listed below in Table 1. The incubation time will vary depending on the strain of prion used. See G. C. Telling et al., *Cell* 83:79–90 (1995 ). The following table summarizes exemplary mice strains and inoculum:

Inoculum (A) Tg(HuPrP)/FVB mice inoculated with sporadic or infectious CJD sCJD(RG)
sCJD(EC)
iCJD(364)
iCJD(364)$^C$
sCJD(MA)

(B) Tg(HuPrP)/$Prnp^{0/0}$ mice inoculated with sporadic or infectious CJD sCJD(RC)
sCJD(RG)
iCJD(364)
iCJD(364)$^C$
sCJD(MA)
sCJD(RO)

(C) Tg(HuPrP)/$Prnp^{0/0}$ mice inoculated with inherited GSS or CJD

GSS(JJ,P102L)
fCJD(LJ1,E200K)
fCJD(CA,E200K)
fCJD(FH,E200K)

Homogenate of either the brain of a single infected animal or a plurality of animals infected with the same inocula is used to inoculate a larger number of Tg(HuPrP)/$PrP^{0/0}$ mice, which are then followed for signs of infectivity. Depending on the level of prion protein desired in the standard, animals can be killed at a specific time following innoculation and/or when they exhibit a specific physiological response to infection, e.g. a certain degree of ataxia. These brain samples are pooled, and a new batch of Tg(HuPrP)/$PrP^{0/0}$ mice inoculated with the homogenate. This continues, with a new batch of mice used for the production of the standard being inoculated with inocula from a preceding generation, and most preferably from the infected mice directly preceding the new generation. Alternatively, several generations of mice can be infected with the inocula of a single earlier generation. This procedure allows the standardization of the prion concentration of the standard while diminishing the background due to genetic variation of the prion preparation.

Human prion proteins are isolated from the mice using techniques available in the art. See e.g. Prusiner et al., *Cell* 35:349–358 (1983). These proteins can be used to augment a normal human brain preparation for use as a standard. Total protein concentrations are determined for the human brain homogenate as described above in Example 2, and then the preparation can be spiked with the human prion isolates. Spiking a brain homogenate to create a standard allows the exogenously added form of the prion to be found in a relative concentration to the overall protein concentration found in the sample. The sample can then be tested for total prion concentration, which would constitute levels of both endogenous prion concentration and exogenous prion concentration.

Once the standard has been generated and the critical properties determined, this standard can be used to harmonize data between assays. For example, the comparative prion assay and direct prion assays may result in different assay values for a human sample. By performing each of these assays on the standard with known properties, a correction value may be determined to allow harmonization. The human prion standard is diluted into multiple concentrations: a 1:2 dilution, a 1:5 dilution, a 1:10 dilution and a 1:50 dilution. The competitive and direct assays are performed on each of the dilutions of the human prion standard. The results of the assay values retrieved for each dilution are used to determine a correction value to harmonize the data to reflect the determined true value of prion concentration in the sample.

Example 5

Multitissue Prion Standards

A number of standard brain samples from mice prepared as in Example 3 are used in the mold to create a multispecies prion standard for use in testing reagents for specificity and cross-reactivity. Standardized prion preparations from Tg(SHaPrP)/Prnp$^{0/0}$, Tg(HuPrP)/Prnp$^{0/0}$, Tg(ShePrP)/Prnp$^{0/0}$, and Tg(BovPrP)/Prnp$^{0/0}$ mice, each infected with the appropriate strain of prion, are used as the tissue rods in the multitissue preparation. As a control, standardized preparations from each strain of transgenic mice not infected with prion can be used as a negative control. In addition, brain samples from physiologically normal hamsters, humans, sheep and cows can be used in the multitissue standard as a further control. Each of these tissues may be removed from paraffin blocks, may be fresh tissue or, preferably, the tissue is fixed in any of a variety of tissue fixatives known by those in the art. For an example of preparation of tissues for this purpose see Battifora, *Lab Invest* 55:244 (1986). Straight rods of tissue of uniform thickness may be obtained using a multiblade microtome knife.

A tissue embedding mold is created using the techniques as described in Battifora and Mehta, *Lab. Invest* 63:722–724 (1990). Briefly, the mold is a shallow trough containing parallel ridges separating rectangular grooves. The prion standard tissue rods are placed within the grooves in the mold, and 3% agar at a temperature of 60° C. is poured over the tissue rods. The agar is permitted to solidify over a cold plate, and the gels containing the embedded tissue rods is removed from the mold. The multi-sample block can then be sectioned for use in screening reagents, testing for antibody specificity, and the like.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A brain homogenate, comprising:

prions obtained from a plurality of transgenic mice, said mice having a genome comprising two ablated endogenous PrP alleles and an operatively inserted PrP transgene encoding a PrP sequence from a genetically diverse mammal; and a carrier;

wherein the preparation comprises prions (a) which infect and cause disease in the genetically diverse mammal, (b) which are of a known strain, and (c) which are present in a known amount, and further wherein the carrier is of a composition which is different from brain tissue of the genetically diverse mammal and which comprises brain tissue of the transgenic mice.

2. The homogenate of claim 1, wherein the known amount is a known number of infectious units.

3. The homogenate of claim 1, wherein the concentration of prions is known.

4. The homogenate of claim 1, wherein the carrier comprises water.

5. The homogenate of claim 1, wherein the carrier comprises brain tissue from the genetically diverse mammal.

6. The homogenate of claim 1, wherein the prions in the preparation consist essentially of prions of a single strain.

7. The homogenate of claim 6, wherein the strain has a polymorphism selected from the group consisting of: human M129, human V129, human F219, human K219, sheep R171, sheep E171, sheep A136, sheep V136, a bovine 5 octarepeat polymorphism, and bovine 6 octarepeat polymorphism.

8. The homogenate of claim 6, wherein the strain is human and has a pathogenic mutation selected from the group consisting of: a 2 octarepeat insert, a 4 octarepeat insert, a 5 octarepeat insert, a 6 octarepeat insert, a 7 octarepeat insert, an 8 octarepeat insert, a 9 octarepeat insert, P102L, P105L, A117V, D178N, V180L, F198S, E200K, V210I, D217R, M234A, and a stop codon at 145.

9. The homogenate of claim 1, wherein the prions are of a plurality of different known strains.

10. The homogenate of claim 1, wherein the prions are obtained from 10 or more animals.

11. The homogenate of claim 1, wherein the prions are obtained from a transgenic mouse comprising a genomic manipulated to express a high copy number of the exogenous PrP gene, and wherein the host animal spontaneously forms prions that normally infect the genetically diverse mammal.

12. The homogenate of claim 1, wherein the prions are uniformly dispersed in the preparations.

13. The homogenate of claim 1, wherein the transgenic animal is a mouse selected from the group consisting of: Tg(IIuPrP)/Prnp$^{0/0}$, Tg(MIIu2M)/Prnp$^{0/0}$, Tg(HuPrP$^{CJD}$)/Prnp$^{0/0}$, Tg(SHaPrP)/Prnp$^{0/0}$, and Tg(BovPrP)/Prnp$^{0/0}$.

14. The homogenate of claim 1, wherein the transgene is a chimeric transgene comprised of mouse sequences and sequences from a genetically diverse mammal.

15. The homogenate of claim 1, wherein the concentration of the prions in the homogenate is augmented by the addition of isolated prion protein.

16. The homogenate of claim 1, further comprising:

isolated exogenous prions from a second plurality of transgenic mice genetically manipulated to allow infection by a different strain of prions that normally only infect a genetically diverse mammal, said mice infected with prions that infect the second genetically diverse mammal.

17. The homogenate of claim 16, wherein the prions from the first plurality of mice are infectious to a different species than the prions from the second plurality of mice.

18. The homogenate of claim 17, further comprising brain homogenate from the second genetically diverse mammal.

19. A method for preparing a prion protein standard comprising the steps of:

providing a plurality of transgenic mice having a genome comprising two ablated endogenous PrP alleles and an operatively inserted exogenous PrP gene transgene encoding PrP sequences from a genetically diverse mammal;

inoculating the transgenic mice with a composition comprising a known amount and strain of prions which infect the genetically diverse mammal;

incubating the transgenic mice until they exhibit sufficient symptoms of prion infection;

harvesting the brain tissue from the transgenic mice exhibiting sufficient symptoms of prion infection; and homogenizing the harvested brain tissue from the transgenic mice;

wherein the prion protein standard comprises a known amount of prions.

20. The method of claim 19, wherein the known amount of prions of the prion protein standard is a known number of infectious units.

21. The method of claim 19, wherein the number of infectious units is between 0.1 and about 100.

22. The method of claim 21, wherein the number of infectious units is between about 1 and about 10.

23. A method of calibration of a prion protein assay, comprising the steps of:

providing a prion protein standard prepared according to the method of claim 19;

determining a first prion protein concentration in the prion standard by a first assay method;

subjecting a portion of the standard to a second prion protein assay to determine a second prion protein assay value for the standard;

determining a correction value for the second prion protein assay based on the first concentration; and adjusting the second prion protein assay value to reflect the first concentration of prion protein in the standard;

wherein the second prion protein assay is calibrated by adjusting the assay value to reflect the first concentration of prion protein in the standard.

24. The method of claim 23, wherein the assay is calibrated using a plurality of standards with different prion protein concentrations.

25. The method of claim 23, further comprising the steps of:

subjecting a portion of the standard to a second prion protein assay to determine a second assay value for the standard;

determining a correction value for the second assay based on the first concentration; and adjusting the second assay to reflect the first concentration of prion protein in the standard; and comparing the adjusted levels of prion protein in each assay;

wherein the assays are calibrated with respect to one another by adjusting the assay values detected by each assay to reflect the first prion protein concentration.

26. A prion protein standard kit, comprising a plurality of prion protein standard prepared according to the method of claim 19, each preparation comprising prions (a) which infect and cause disease in a known species of mammal, (b) which are of a known strain, and (c) which are present in a known amount.

27. The kit of claim 26, wherein each prion protein standard contains a different amount of prions having the ability to infect and cause disease in the same species.

28. A kit of claim 27, wherein each prion protein standard contains a different amount of a single strain of prion.

29. The kit of claim 26, where each prion protein standard has a same known amount of a different prion strain.

30. The kit of claim 29, wherein each prion strain has the ability to infect and cause disease in a different species.

31. The kit of claim 26, wherein each preparation has one infectious unit of prions.

\* \* \* \* \*